(12) United States Patent
Eisenson

(10) Patent No.: US 6,426,213 B1
(45) Date of Patent: Jul. 30, 2002

(54) SPERM ANALYSIS SYSTEM

(75) Inventor: Henry L. Eisenson, San Diego, CA (US)

(73) Assignee: Progeny Systems, LLC, San Diego, CA (US)

( * ) Notice: Subject to any disclaimer, the term of this patent is extended or adjusted under 35 U.S.C. 154(b) by 0 days.

(21) Appl. No.: 09/622,627

(22) PCT Filed: Feb. 19, 1999

(86) PCT No.: PCT/US99/03669

§ 371 (c)(1),
(2), (4) Date: Jan. 9, 2001

(87) PCT Pub. No.: WO99/42557

PCT Pub. Date: Aug. 26, 1999

Related U.S. Application Data
(60) Provisional application No. 60/075,216, filed on Feb. 19, 1998.

(51) Int. Cl.[7] ............................................. C12M 1/34
(52) U.S. Cl. .......................... 435/288.7; 435/288.1; 435/808; 422/102; 356/440; 356/442; 356/246; 73/864.11
(58) Field of Search .............................. 435/2, 30, 39, 435/40, 288.1, 288.4, 288.7, 305.2, 309.1, 808; 422/100, 102, 82.05, 82.09; 436/63; 356/29, 39, 343, 440–442, 246; 250/328, 428, 461.2; 73/864.11; 359/398

(56) References Cited

U.S. PATENT DOCUMENTS

| | | | | |
|---|---|---|---|---|
| 3,713,985 A | * | 1/1973 | Astle | |
| 3,732,079 A | * | 5/1973 | Davis | |
| 4,420,254 A | * | 12/1983 | Smeaton | |
| 4,622,208 A | * | 11/1986 | Namba et al. | |
| 4,632,562 A | * | 12/1986 | Dupree et al. | |
| 4,824,247 A | * | 4/1989 | True et al. | |
| 4,880,732 A | * | 11/1989 | Resli et al. | |
| 4,896,967 A | * | 1/1990 | Douglas-Hamilton et al. | |
| 5,116,125 A | * | 5/1992 | Rigler | |
| 5,249,584 A | * | 10/1993 | Karkar et al. | |
| 5,402,240 A | * | 3/1995 | Thistlethwaite et al. | |
| 5,430,542 A | * | 7/1995 | Shepherd | |
| 5,756,304 A | * | 5/1998 | Jovanovich | |
| 6,238,874 B1 | * | 5/2001 | Jarnagin et al. | |

* cited by examiner

*Primary Examiner*—William H. Beisner
(74) *Attorney, Agent, or Firm*—Procopio, Cory, Hargreaves & Savitch, LLP

(57) ABSTRACT

A sperm analysis system has a sperm sample carrier (20) and "reader" module. The sperm sample carrier includes: 1) a shank (24) defining a chamber (26) with an opening for ingress and egress of a sperm sample; a manually operated pump (28) for aspirating a sample of sperm into the chamber (26), and a plurality of distinct photon paths (34) intersecting and passing through the chamber (26). The module includes: a processor responsive to an actuation signal from an operator, a photon source, e.g. a light source, energized by the processor in response to the actuation signal, for sending respective beams of photons through each of the photon paths, a plurality of photosensors, one for each photon path, each for producing a signal indicative of the occurrence and frequency of perturbations in the beam of photons passing through said each's respective photon path and communicating the signal to the processor, and an algorithm run by the processor for processing the plurality of photosensors signals to produce a quantified figure of merit indicative of the motility of sperm within the chamber.

21 Claims, 6 Drawing Sheets

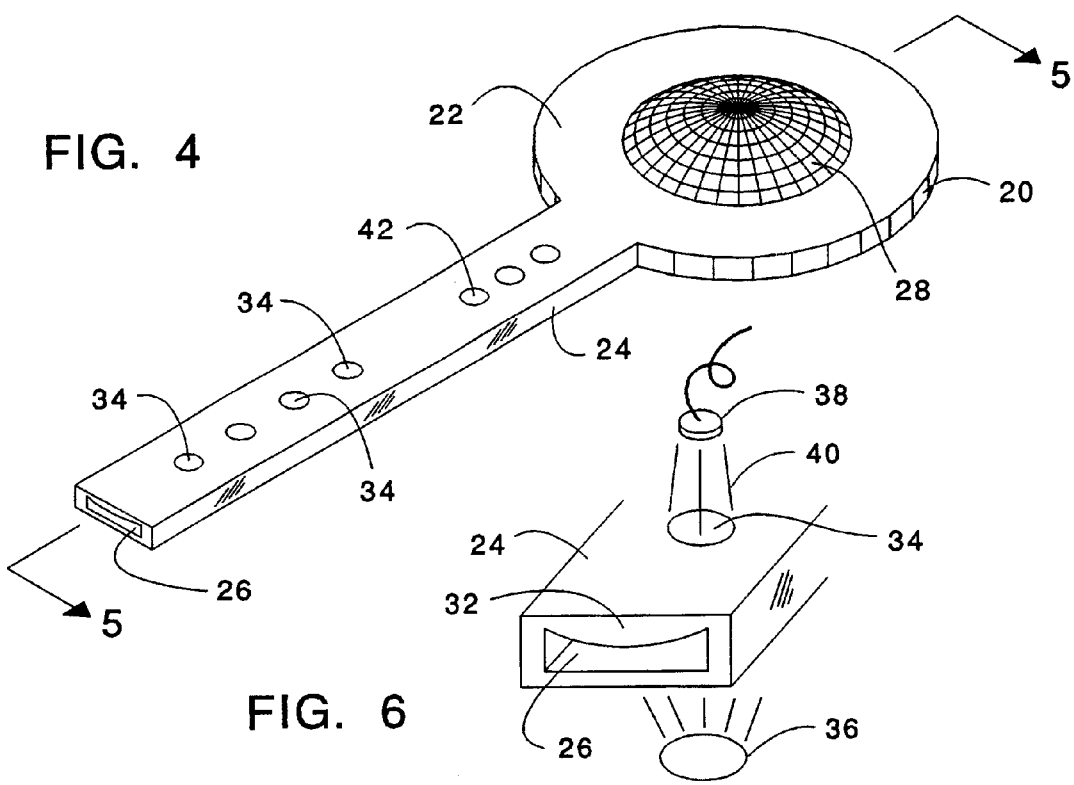

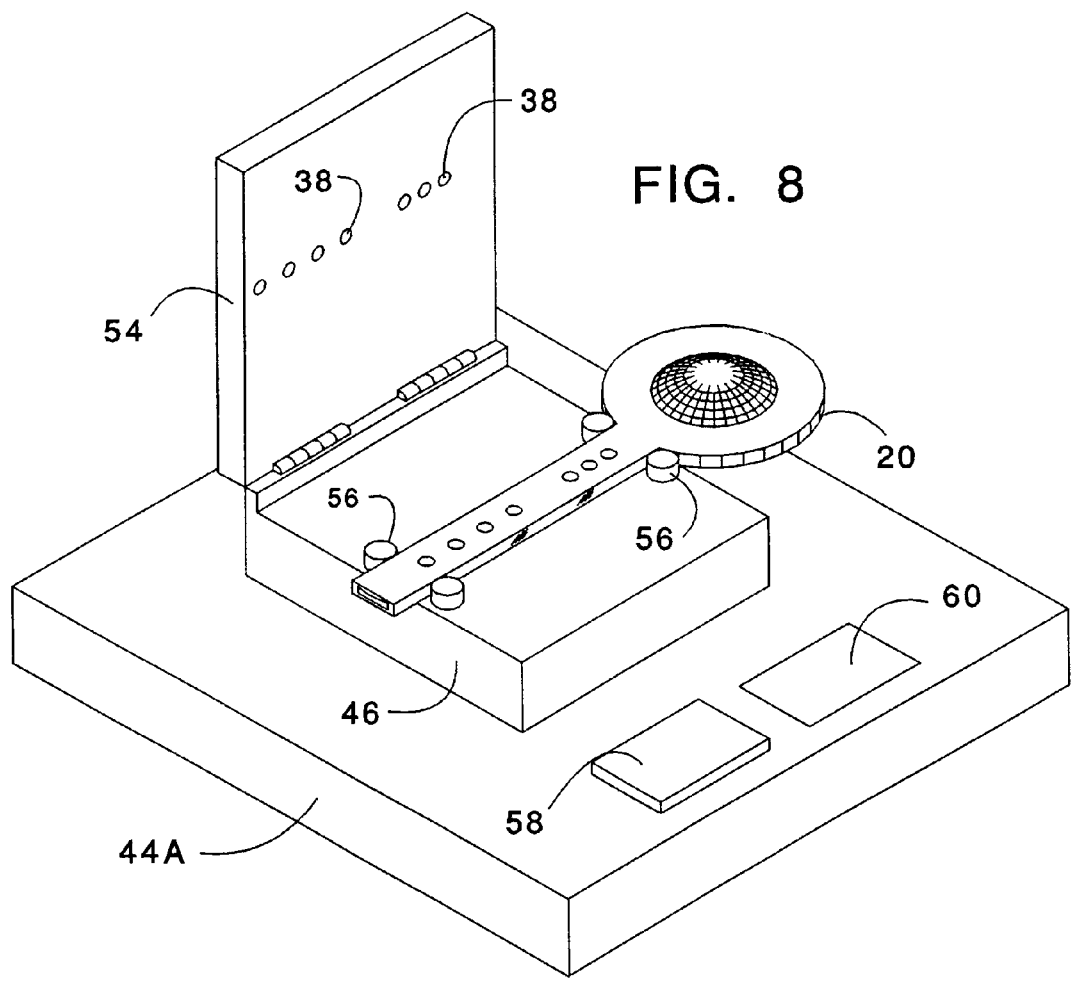
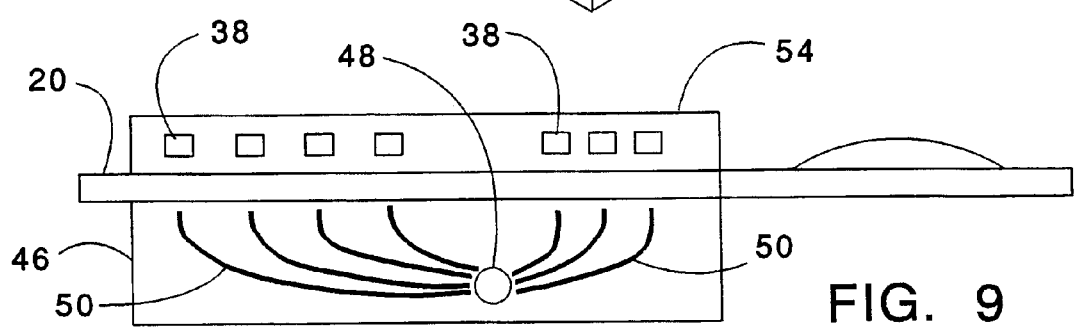

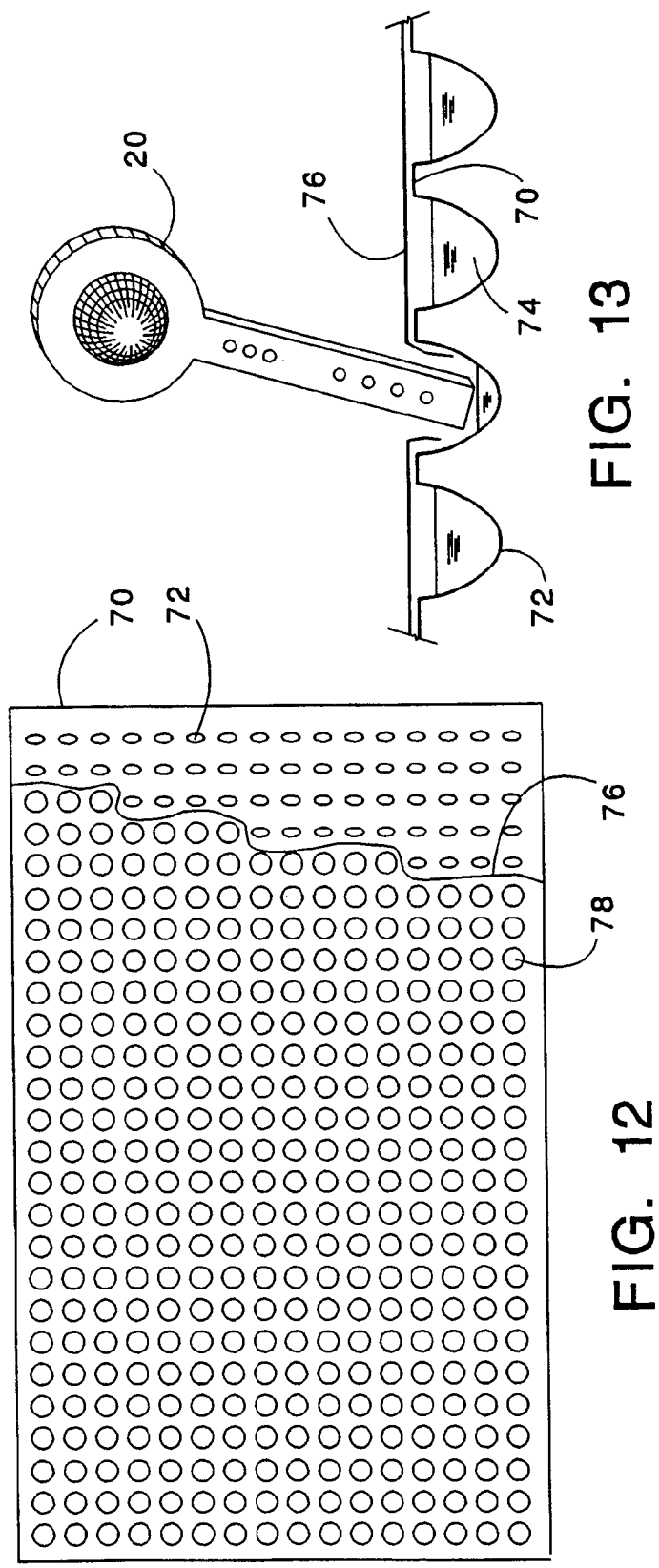

SPERM ANALYSIS SYSTEM

This application claims the benefit of U.S. Provisional Application No. 60/075,216, filed Feb. 19, 1998.

BACKGROUND OF THE INVENTION

This invention relates in general to devices and methods for quickly and inexpensively analyzing the impregnation potential, or fertility, of a sperm sample in a non-laboratory setting, and in particular to such devices and methods in which a user performs only a few simple mechanical steps to provide sperm input to a computerized module which automatically performs an analysis and provides a resultant figure of merit.

Over the past few decades, animals in general-from fish to humans-have demonstrated a substantial reduction in general fertility. In most species, the problem appears about equally in the male and the female partner. The decline has been attributed to pollution of the world's environment, global warming, contra-Darwinian medical practices, selection of desirable traits without regard for fertility, and many other factors. The reality of that decline is certain and has been measured worldwide, but its causes are unclear.

In species that are important to humans the decline is often our fault. Some food animals have been carefully bred to meet specific tastes of humans, but at the expense of fertility of that species. As examples, turkeys and chickens bred to maximize white-meat production do so at the demonstrable expense of fertility. Even pets and work animals, selected over many generations for appearance or performance characteristics, have seen significant deterioration of fertility. Subfertility in poultry, cattle, pigs, and other food animals creates at least a billion dollar annual loss worldwide.

Regardless of the species, there are several techniques by which a female partner can be checked for fertility, including physical examination, hormonal workups, egg harvests, and other testing, but there are only two measurement sets by which a male partner can be checked: "sperm count" and chemistry. By far the majority of subfertile males can be identified by characterizing their sperm count. It is extremely rare to discover a male with a chemical defect that is not accompanied by another problem identifiable by a sperm count. To determine "sperm count," some form of magnification is used to increase the apparent size of the spermatozoa, or sperm cells, and then they are "counted" by a human or a computer. In some species there are more than one billion cells per milliliter. The fast-moving cells, therefore, are very small and difficult to quantify even with a microscope. Often, an optical grid is used to divide the sample into segments to facilitate accuracy. Whether by a human observer or a computer, the cells are counted to determine (1) the total number per unit volume, (2) the degree of motility, and sometimes (3) the general shape of the cells, or "morphology." The result of a sperm count is usually a report that includes these factors plus others, such as volume, color, pH, etc., that may reflect the general health of the male. But the overwhelmingly important single measurement, in virtually all species, is the number of motile cells available to penetrate the egg. For the purpose of this document, "sperm count" refers to "healthy sperm count": the concentration of cells capable of impregnating an egg.

As for treatment of subfertility, there are proven treatments by which the fertility of a female can be enhanced, including a spectrum of hormones; among food animals, certain veterinary drugs are available that work upon the female to increase the average litter size. But male fertility is another matter entirely. Regardless of species and despite the efforts of medical and veterinary sciences, only a very small percentage (<1–2%) of subfertile males have conditions which can be treated to increase sperm count. In almost all cases, and in all species, there is no successful therapeutic approach to male subfertility.

In typical food animals, there is competition among the males to mate with multiple females. A subfertile male that is otherwise dominant may seek to impregnate many females, driving away less dominant but potentially more fertile competitors. This results in poor reproductive performance of multiple females and becomes very expensive. In veterinary fertility medicine, particularly as it applies to food animals, subfertility has a direct and calculable impact. It is therefore most advantageous to be able to quickly and inexpensively measure the impregnation potential of the males in a food stock so that the subfertile males can be culled from the stock, leaving only the fertile males to compete for the females.

The prior art for determining the impregnation potential or fertility of a semen sample basically includes only computer assisted semen analysis ("CASA"), microscopy, a device called the Sperm Quality Analyzer ("SQA") and biochemical assays performed in a laboratory and therefore inappropriate for real-time analysis in the field. CASA is achieved with a microscope, one or more video cameras, video image conversion hardware, a computer, and one or more displays. CASA systems have been developed by three companies, at prices ranging from $30,000 to more than $50,000. They are generally considered too expensive for even hospital clinical laboratories, and are certainly too costly for food animal breeders, e.g. chicken breeders. As for microscopy, a conventional laboratory microscope is used, usually in conjunction with a device that presses the sample into a very thin film against a finely etched grid to facilitate counting. This method is time consuming, expensive especially in terms of labor, and the results are subjective—based on a person's ability to count the density of spermatozoa in a unit volume.

The SQA is a computerized device that has been used by sperm banks, fertility clinics, and laboratories to measure certain characteristics of sperm. A sperm sample is drawn into a transparent capillary with precise internal dimensions. After a sample rises into the capillary, the carrier is inserted into an elongated slot wherein a calibrated light is directed by a fiberoptic conduit to illuminate a small segment of the capillary. At a side of the capillary opposite the light is a photosensors which senses the occurrence and frequency of very small perturbations in the light passing through the capillary. These perturbations, which are caused by movement of the sperm cells within the capillary, are converted to digital data and communicated to a computer. The computer applies a known algorithm to the data and produces a numerically expressed Sperm Motility Index (SMI) which is on an arbitrary scale which reflects overall sperm quality or relative fertility of the sperm samples. SMI values for humans range from 0 in complete asthenzoospermic azoospermic patients to over 160 SMI units in good quality sperm. It is essentially a measurement of the number of motile cells and the nature of their motility.

This invention uses some of the principles of the SQA (optically sensing motion of sperm within a certain amount of semen) to produce a fertility figure of merit, e.g. an SMI or similar datum, but overcomes many of the problems encountered by the SQA. Moreover it includes processes which are novel and unique over those used in the SQA. It also provides features not seen or known in connection with the SQA, for example, features which make this invention adaptable to unclean animal environments. In this regard, the SQA was designed for a laboratory environment and has serious problems with contamination of the slot into which the carrier is inserted to make a reading. Minute specks of dirt can easily get into the slot and cause erroneous readings, and the device has to be significantly disassembled to clean the slot. This invention is much less likely to be contaminated, and if so, it is quickly and easily cleanable. This invention also provides a plurality of portable measurement modules each pluggable into a case for charging and interfacing with at least a printer and display. Also, the SQA takes forty seconds to provide an SMI value because it performs its basic test four times for accuracy. This invention provides a novel, disposable capillary carrier which enables a measurement module to perform multiple tests in parallel, thus reducing the time per analysis to a fraction of the SQA's time, enhancing practicality in the food animal industries.

This invention is the most cost effective technique to determine male fertility whether it is used for humans or animals. This is due to the need for only inexpensive equipment (as will be seen), minimal user training, low per-test consumables cost, and rapidly displayed results. The last is very important because in the fertility measurement business, time is money. Another important advantage is the complete lack of subjectivity in achieving results. The computer makes all judgements. Multiple parallel samplings by laboratory scientists produces a broad bell-shaped curve of results because of inherent subjectivity, but with this invention parallel measurements are very consistent and the results are defined by a "spike" rather than a bell curve.

An example of how this invention can be advantageous concerns the chicken industry. "Broilers" are those chickens raised to become meat. The U.S. broiler industry hatches approximately 9 billion birds per year, at an efficiency much higher than anywhere else in the world. These 9 billion eggs hatch from about 10.7 billion laid by approximately 70 million hens, which are fertilized by about 7 million roosters. But a significant percentage of the roosters are subfertile, resulting in a loss of about 16% of all eggs laid, or about 1.7 billion. Until now there has been no practical, cost effective way to differentiate between fertile and subfertile roosters, hence the industry has heretofore achieved only an 84% hatchability rate. However, a study done at the Mississippi State University by Chris McDaniel, PhD, using an SQA found positive correlations of the SMI with sperm-egg penetration and live sperm concentration, but negative correlation with the percentage of dead sperm. Dr. McDaniels concluded that these correlations indicated that the SMI can used to improve broiler breeder males for fertilizing potential. During his study, Dr. McDaniel developed what is now known as the "McDaniel protocol" which defines an SMI scale to be used for roosters and also defines the ratio a rooster sperm sample must be diluted. Dilution is necessary because rooster semen has concentrations of billions of cells per milliliter, the dilution moves the concentration into the most linear range of the instrument. The preferred dilution is one part sperm to five parts diluent which is a simple saline solution. In this regard, this invention also includes a means for quickly, cleanly, accurately, and inexpensively diluting a rooster's or any other species' sperm sample in the appropriate ratio.

In summary, this invention presents a simple, cost-effective, and proven methodology by which subfertile roosters, or the males of any other species, can be identified and culled from a breeding group, thus improving fertility and the resulting number of progeny.

Other advantages and attributes of this invention will be readily discernable upon a reading of the text hereinafter.

SUMMARY OF THE INVENTION

An object of this invention is to provide a portable system for quickly, accurately and inexpensively analyzing on-site the impregnation potential, or fertility, of multiple male animals, "on-site" meaning where the animals are kept, e.g. a barn, hen house or even in a field.

A further object of this invention is to provide such a system in which a user performs on-site only a few simple mechanical steps (e.g. aspirating semen into a carrier, inserting the carrier into a portable analysis module, pushing a button) to quickly get an indication of fertility.

A further object of this invention is to provide a system as described in the preceding paragraph which produces a sperm motility index ("SMI") value or other index of relative fertility.

A further object of this invention is to provide a system as described in the two preceding paragraphs which can be used in unclean animal environments.

A further object of this invention is to provide a system as described in the three preceding paragraphs in which individual sperm samples are collected in inexpensive sperm carriers which are placed in a measurement module for analysis and then preferably discarded.

A further object of this invention is to provide a system as described in the preceding paragraph in which the sperm carrier is further designed to permit calibrated dilution of a sperm sample within it.

A further object of this invention is to provide a system as described in the preceding paragraphs in which a plurality of measurement modules are pluggable into a module carrier for energizing and for interfacing the modules to at least a printer and display.

A further object is to a system as described in the preceding paragraphs which has at least one additional optical path through the carrier for obtaining readings other than motility, e.g. for obtaining a semen-absent reading for measuring sperm density along with motility.

A further object is to a system as described in the preceding paragraphs which is further capable of measuring the sperm density of a semen sample along with motility.

A further object of this invention is to provide a system as described above in which a sample carrier which exhibits a code readable by a processor for identifying the species from which the sample was obtained.

A further object of this invention is to provide a system as described in the preceding paragraph in which the code is made illegible to the processor after a time by action of a semen sample solution.

These and other objects, expressed or implied, are accomplished by a sperm analysis system which has a sperm sample carrier and "reader" module. The sperm sample carrier includes: (1) a shank defining a chamber and an opening into the chamber for ingress and egress of a sperm sample, (2) a manually operated pump for aspirating a sample of sperm into the chamber, and (3) a plurality of distinct photon paths intersecting and passing through the chamber. The module includes: (1) a processor responsive to an actuation signal from an operator, (2) a photon source, e.g. a light source, energized by the processor in response to the actuation signal, for sending respective beams of photons through each of the photon paths, (3) a plurality of photosensors, one for each photon path, each for producing a signal indicative of the occurrence and frequency of perturbations in the beam of photons passing through said each's respective photon path and communicating the signal to the processor, (4) an algorithm run by the processor for processing the plurality of photosensors signals to produce a quantified figure of merit indicative of the motility of sperm within the chamber, (5) and means for communicating to an operator the figure of merit. Preferably the photon source means comprises a light source and a plurality of photon conduits, e.g. fiber optic cables, each conduit receiving photons from the light source and directing them to enter one end of a respective photon path, a respective photosensors being disposed at an opposite end of the path to sense the photons leaving the path. Preferably the system also includes indicia disposed on the sperm sample carrier for conveying to the processor the biological classification of a donor of a sperm sample within the carrier's chamber. Preferably the system also includes a tray defining a plurality of closed cavities, each cavity containing a precise amount of semen diluent. Preferably the cavities are closed by a frangible seal which can be breached by the shank of a carrier to expel a semen sample from the carrier into the diluent and to stir them together, the mixture then being aspirated in the carrier for testing.

BRIEF DESCRIPTION OF THE DRAWINGS

FIG. 4 is a pictorial view of a sperm sample carrier according to this invention.

FIG. 5 is a cross-section of the sample carrier of FIG. 2 taken along line 5—5.

FIG. 6 is a functional diagram of the optics of this invention.

FIG. 7 is a cross-section along a same line as in FIG. 5 but showing the sample carrier at a pre-manufactured stage.

FIG. 8 is a pictorial view of an analysis module according to this invention.

FIG. 9 is a functional diagram of the optical characteristics of an analysis module according to this invention.

FIG. 12 is partially cut-away plan view of a diluent tray according to this invention.

FIG. 13 is a pictorial view illustrating how a sperm sample is diluted according to this invention.

DESCRIPTION OF THE PREFERRED EMBODIMENT

Figure 1:
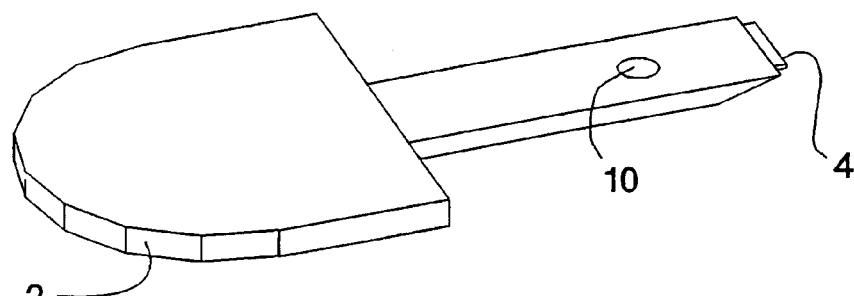
FIG. 1 is a pictorial view of a prior art SQA sperm sample carrier.
Figure 2:
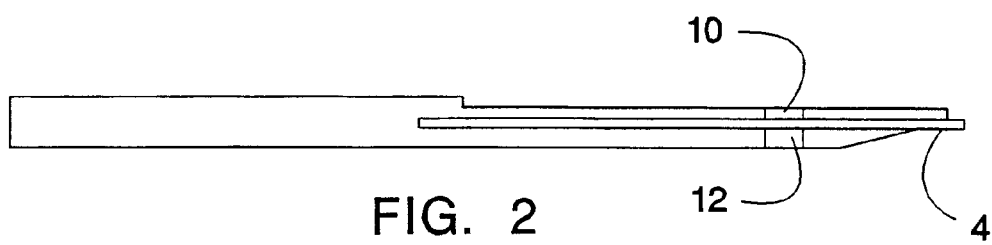
FIG. 2 is median cross-section of the sample carrier of FIG. 1.
Figure 3:
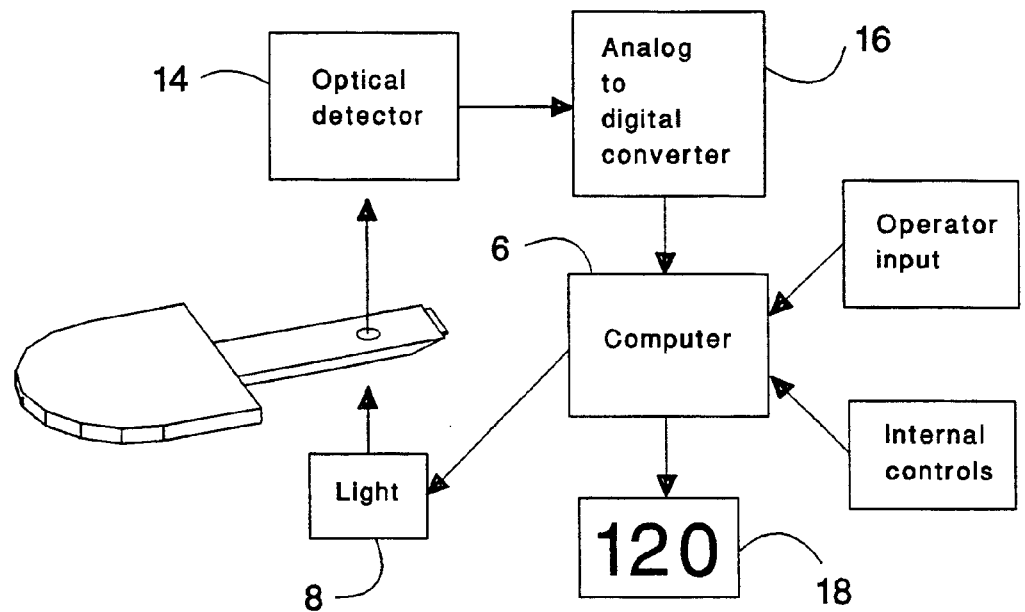
FIG. 3 is a diagram of how the prior art SQA operates.

Referring to FIGS. 1–3, a prior art SQA is shown to have a sperm sample carrier 2 in which is mounted a capillary 4. A sperm sample is drawn into the carrier by capillary action. The carrier is inserted into a slot (not shown) of a laboratory desktop analysis computer 6. When a test is actuated by an operator input, the computer energizes a light 8 which shines through the capillary via holes, 10 and 12, defined by the carrier. The light passing through the capillary is sensed by an optical detector 14. The detector's response to the light is digitized 16 and sent to the computer which applies an algorithm. This is repeated four times, and the results of the four tests are compared and integrated to produce an SMI value for the subject sample. The value is then displayed 18 for an operator. This process takes at least one minute (ten seconds per test plus setup time) for each sample.

Referring to FIGS. 4–6, a sperm sample carrier 20 according to this invention is illustrated to have a disc-like handle 22 and an elongated shank 24. The shank defines a longitudinal channel 26 into which a sperm sample is drawn preferably by a vacuum created by actuation of a resilient, flexible bulb 28 in the center of the handle. The carrier is preferably plastic and its preferred overall dimensions are: 7 cm total length, 2 cm diameter for the handle, 2 mm thick with the channel being about 1.5 mm ×0.3 mm. Beneath the bulb is a pump chamber 30 communicating with the channel 26. When the bulb is pressed down it decreases the volume of the chamber and forces air out of the chamber and the channel, and when the bulb returns to its memory shape it creates a temporary vacuum which aspirates the sample into the channel up to a mark on the channel. This is a much faster process then simply waiting for the sample to be drawn in by capillary action. The vacuum drawing method works even for very viscous semen, such as rooster semen, whereas capillary action is ineffective or unreliable in such situations. The extent to which the volume of the chamber can be decreased is preferably controlled by a spacer 32 which can be, for example, molded ridges projecting from the base of the chamber 30. The channel inner dimensions are such that it can hold a sample once it has been drawn in. As will be explained below, this pumping action also provides a way of conveniently temporarily aspirating the sperm sample to dilute it, and then draw the dilute sample back into the channel.

Referring to FIGS. 4 and 6, the carrier is preferably made from clear plastic but its top is painted with a logo and other information, and generally rendered opaque except for certain orifices defined by the paint for allowing light to pass entirely through it. Four of the orifices 34, are used to make optical measurements. Light sources 36 shine into the channel on one side, and optical detectors 38, one aligned with each optical orifice 34, on the opposite side sense the light 40 passing through the orifices. Preferably there are a plurality of such orifices to allow a like plurality of tests to be performed in parallel, rather than consecutively as in the SQA. Preferably there are a plurality of binary-coded optical orifices 42 (illustrated herein by way of example only to be a binary pattern of "111") to create a multiple-bit pattern to identify the species from which the semen has been obtained. Carriers for each species are made with differing bit patterns. For example the illustrated code could mean that the sample is from a rooster, whereas a code of "011" could mean that the sample came from a bull. The computer uses this information to select a corresponding calibration.

Referring to FIG. 6, the lateral cross-section of the top 32 of the channel 26 has a lens shape to help focus the light passing through the optical orifices from below. The lens shape is designed to ensure that a greater amount of light from a larger cross-section of the sample reaches the optical detector, thus increasing the amount of information available for calculation.

Referring to FIG. 7, the sample carrier 20 is preferably molded as a hollow shank 24 with the handle 22 being open like a clamshell. The clamshell end is then folded closed and ultrasonically welded. The assembly is then silk-screened or otherwise printed to make appropriate portions opaque and to carry an operating message. Preferably it is packaged with a paper cover that is peeled away and discarded just before use. The paper protects the entry of the channel 26, the ink-defined optical orifices, and the plastic until used.

Referring to FIGS. 8 and 9, an analysis module 44A is shown to include a sperm sample "reader" which has a clamshell configuration for closing upon a located sample carrier 20.

The reader has a base 46 which houses a light source 48, and a plurality of fiberoptic conduits 50 for conveying light from the source to translucent spots 52 (FIG. 10) which align with respective optical orifices on a carrier being read. The light emanating from these translucent spots passes through the carrier and is sensed by a corresponding plurality of optical detectors 38 disposed in a top 54 of the reader. Preferably the top is attached by spring-loaded hinges and is normally-open because it also functions as a switch which must be closed to initiate an analysis. A carrier being read is precisely located by preferably four pegs 56 in order to properly align the carrier's optical orifices with the translucent spots and optical detectors. Alternatively the module may define a locating groove or seat (not shown) into which the carrier is placed for reading. To read a carrier, the top is closed and a switch 58 is actuated. A computer inside the module performs the analysis and thereafter displays an SMI value via a display panel 60. The clamshell design makes cleaning the optical paths very easy, especially since the optic terminals of the reader, both top and bottom, are flush and hence can be wiped clean without difficulty. Thus the chance of erroneous readings due to contamination of the optical paths is greatly reduced.

Figure 11:
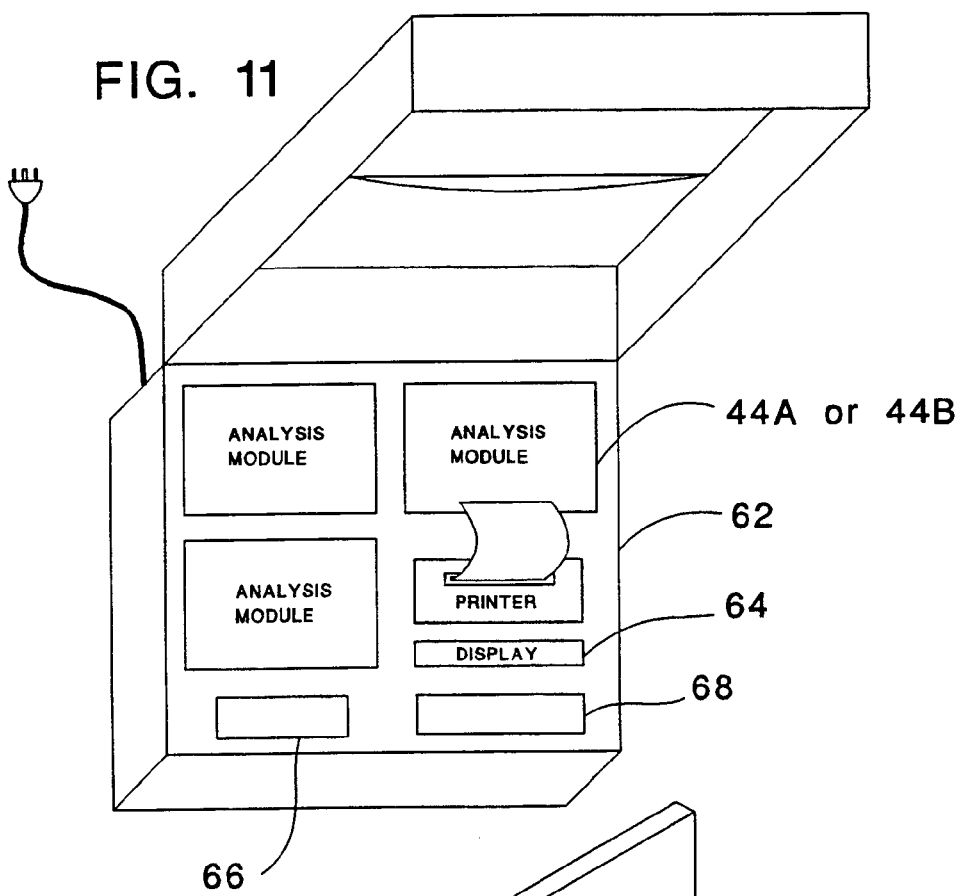
FIG. 11 is a pictorial view of an analysis module carrier according to this invention.
Figure 10:
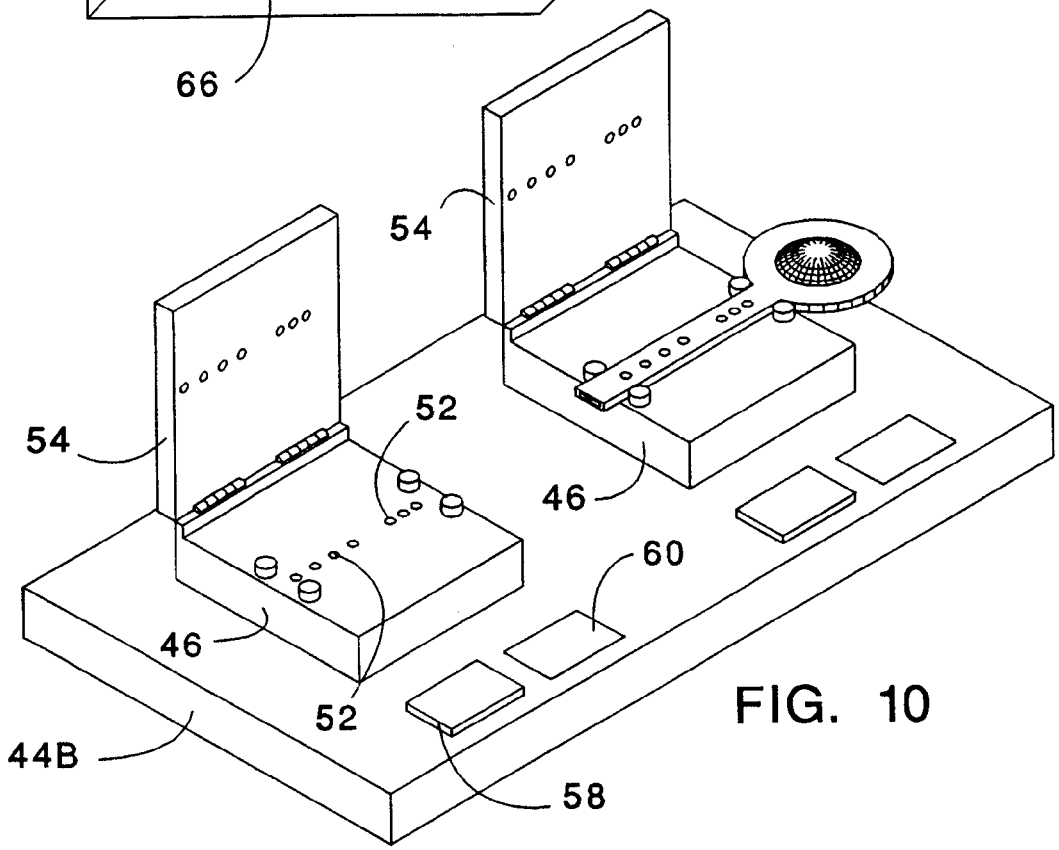
FIG. 10 is a pictorial view of a dual analysis module according to this invention.

Referring to FIGS. 10 and 11, an analysis module can be single-channel 44A, with one optical reader as in FIG. 8, or it can be multiple channel 44B having a plurality of readers, as in FIG. 10. The latter provides even further acceleration of the testing process because the reading of more than one carrier can be overlapped depending on the speed and capabilities of the processor in the module. Preferably each analysis module is powered by a rechargeable battery and completely sealed in a sterilizable package. Battery power is extremely advantageous in animal environments, e.g. hen houses, in which it would be very difficult, if not impossible to lug around an extension cord while trying to catch and draw semen samples from the animals. Portability allows a user to quickly do a test and, based on a given animal's score, decide whether to remove that animal from the breeding stock. Also, the analysis module preferably stores the information in non-volatile flash memory, thereby allowing operators to accumulate all the data from, say, a group of roosters and later print the data.

Referring to FIG. 11, preferably the analysis modules are stored, carried and recharged in a carrying case 62, and when they are returned to the case, the data from each module can be selectively printed, generating cumulative information to support management decisions. As illustrated, the modules, while stored in the case, reside in individual saddles which also inductively or capacitively connect the modules with circuits within the case. While in their respective saddles they are being recharged and are interfaced to the printer or an intermediate processor resident in the case. Preferably each analysis module is inductively coupled to the charging system in the case, and capacitively coupled to a data port in the case, both to avoid contaminating the case and its circuits with contamination picked up by orifices and/or cracks in the module. The case also provides a display panel 64 to display pertinent information, and operator controls for controlling the recharging process 66 and for controlling the printer 68.

Referring to FIGS. 12 and 13, for many species dilution of semen is necessary or preferred for sperm motility measurements. Also, in food animal (particularly poultry) measurements, large numbers of tests are usually conducted simultaneously. So a diluent tray 70 has been developed to provide a fast, easy and inexpensive way to achieve precise dilution. It consists of a planar tray defining a plurality of uniform cavities 72 preferably molded into it. Each cavity contains a precise amount of a saline solution 74 known to the laboratory industry. The amount of saline or other diluent is some multiple of the capacity of the carrier's semen channel (26 of FIG. 5), the multiple depending upon the species and the viscosity of its semen. The entire tray is then covered with a frangible film 76, such as thin aluminum foil, adhesively attached to seal and isolate all cavities. Circular marks 78 on the film cover indicate the precise location of each cavity. To dilute a semen sample in a carrier 20, the carrier's tip is pushed through the foil covering an unused cavity in the diluent tray. The bulb on the carrier's handle is then depressed to expel the semen into the cavity, and therefore into the diluent. The tip of the carrier is then used to stir the sample into the diluent. The resultant mixture is then re-aspirated into the carrier by depressing the bulb to expel any gas or liquid within the channel while tip is immersed in the diluted sample. Relaxing the pressure causes the carrier to aspirate the diluted sample, re-filling the channel. In effect, the carrier operates like an "eye-dropper," permitting expulsion and re-aspiration of samples. The carrier tip then may be wiped clean. The carrier is then placed into an optical reader for analysis.

In operation, each analysis module when actuated, first checks to see if the four optical reading paths in its reader are "clean." It energizes the optical light source and takes a reading from the four optical detectors. If they are all within a normal range, then the module assumes that all four paths are clean. If one or more are without the normal range, the module will flag them as being contaminated. The module then adjusts its analysis sequence accordingly. For example, if all four paths are clean, then it will perform four concurrent analyses, one for each path, and then compare the results to arrive at the SMI or similar datum. If one of the paths is contaminated, it will perform three concurrent analyses via the three uncontaminated paths and subsequently perform a fourth analysis in one of the uncontaminated paths so that once again four readings can be compared to arrive at the SMI. If two of the paths are contaminated, then it will perform two concurrent analyses via the uncontaminated paths and subsequently perform two more to again arrive at four analyses for comparison purposes. Even if three of the four optical paths are contaminated, the module can still perform an accurate analysis by performing four consecutive analyses through the clean path.

It should be noted that the number of individual readings to be compared is primarily determined by the level of accuracy necessary. There may be situations in which four readings are not necessary, or where more than four readings are necessary.

Once the analysis module has determined the clean paths and has set its analysis sequence, an operator places a semen carrier in the optical chamber, i.e. between the pegs as illustrated in FIG. 8. The operator then closes the lid which initiates or at least arms the analysis process and initiates an actual test. At that point, the computer in the module once again turns on the optical light source. The computer then determines the species from which the semen has been extracted by the binary bit pattern on the carrier, and self-calibrates accordingly. If no bit pattern is detected, no test is performed and the computer indicates that the carrier is not valid. From the light passing through the semen sample in the carrier, via the clean optical paths, the computer determines the motility of the sperm using a previously described algorithm. The test data are then stored in non-volatile memory and the result is displayed to permit an operator to make an on-site decision as to the particular male being tested. The module is then ready to test another sample from another male of the species. In this way, an operator can walk through a flock or a herd, or such, and make multiple tests using the same module but with separate carriers for each test. When the unit is returned to the case, the battery in the module is recharged, and the data stored in the module is download preferably to storage in the case, and the data is ready for printing. The operator then optionally selects a print mode and gets a printout of all of the males he or she has tested. Since the case can hold multiple modules there could be multiple operators walking the animal group and testing and collecting data. All the data from all of the modules are then downloaded into the case for subsequent printout or for subsequent transfer to another computer for further analysis.

Figure 14:
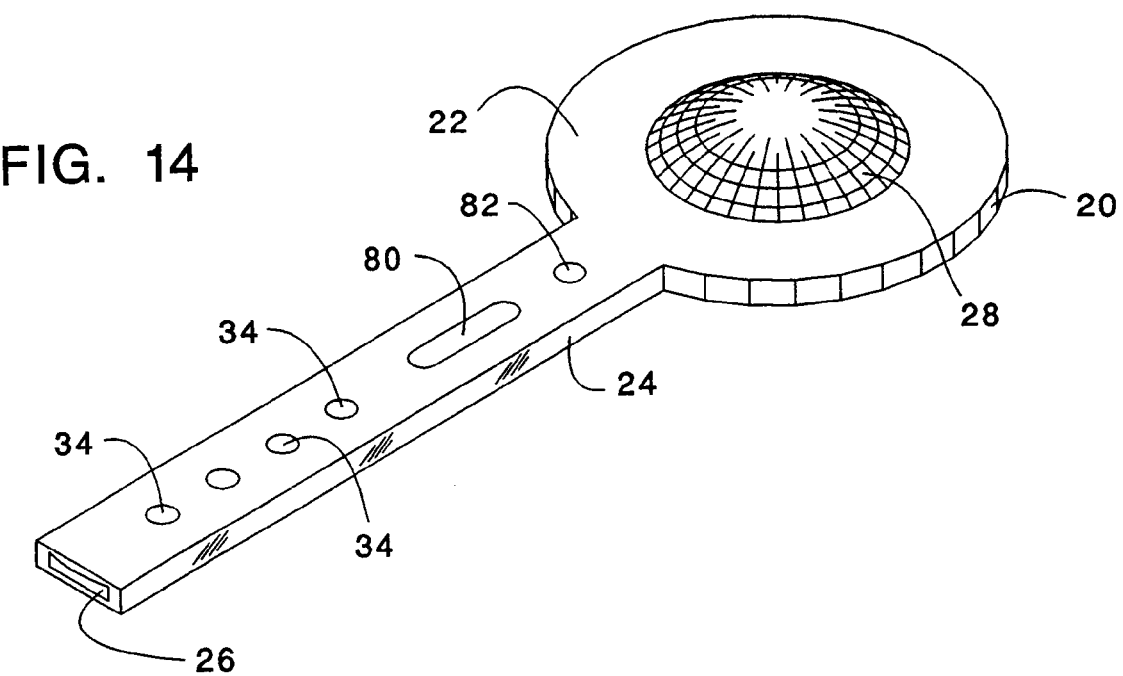
FIG. 14 is a functional diagram of an alternative sample carrier which provides an additional optical path for use in obtaining additional readings, e.g. a semen-absent, reference reading for determining sperm density.

Referring to FIG. 14, it can be seen that the optical, i.e. photon, paths need not be one uniform size but can be larger, as at 80, to create a bigger window through which to sense the sample. For example, a broader cross-section of the channel permits measuring static optical density of the fluids evidenced by relative absorption of light. Also, sperm density can be measured by comparing photodetector signals from a reference optical path 82, a path through a part of the channel without semen and a path through a semen filled portion of the channel. The difference points to total cell concentration. Another way to do this is to getting a reading on an empty carrier and remember the reading to subsequently compare it to a reading from a filled carrier. In either case the densimetry measurement can be used with a motility reading to give a more accurate assessment of sperm fertility.

The foregoing description and drawings were given for illustrative purposes only, it being understood that the invention is not limited to the embodiments disclosed, but is intended to embrace any and all alternatives, equivalents, modifications and rearrangements of elements.

I claim:

1. A sperm analysis system comprising:
    (a) a sperm sample carrier including:
        (1) a shank defining a chamber and an opening into the chamber for ingress and egress of a sperm sample,
        (2) manually operated means for aspirating a sample of sperm into the chamber, and
        (3) a plurality of distinct photon paths intersecting and passing through the chamber;
    (b) a processor responsive to an actuation signal from an operator;
    (c) photon source means, energized by the processor in response to the actuation signal, for sending respective beams of photons through each of the photon paths;
    (d) a plurality of photosensing means, one for each photon path, each for producing a signal indicative of the occurrence and frequency of perturbations in the beam of photons passing through said each's respective photon path and communicating the signal to the processor;
    (e) an algorithm run by the processor for processing the plurality of photosensing means' signals to produce a quantified figure of merit indicative of the motility of sperm within the chamber; and
    (f) means for communicating to an operator the figure of merit.

2. The system according to claim 1 wherein the shank is transparent, and further comprising a coating around the shank rendering it opaque except for a plurality of orifices in the coating, each photon path being defined by a pair of aligned orifices on opposite sides of the chamber.

3. The system according to claim 2 further comprising a wall of the chamber having a lens shape for focusing photons traversing the photon paths.

4. The system according to claim 1 wherein the photon source means comprises a light source and a plurality of photon conduits, each conduit receiving photons from the light source and directing them to enter one end of a respective photon path, a respective photosensing means being disposed at an opposite end of the path to sense the photons leaving the path.

5. The system according to claim 1, further comprising indicia disposed on the sperm sample carrier, the indicia being readable by the processor, the indicia conveying to the processor at least information concerning the biological classification of a donor of a sperm sample within the carrier's chamber.

6. The system according to claim 5 wherein the indicia comprise a subset of the plurality of photon paths, each photon path of the subset conveying a binary bit of information by being either translucent or opaque.

7. The system according to claim 6 wherein each opaque photon path of the indicia subset includes an opaque spot deposited on an inside wall of the semen sample chamber in a position to block photons from traversing the path.

8. The system according to claim 7 wherein the opaque spot disintegrates, after a time, by action of a semen sample in contact therewith, the time being long enough to allow a user to get a motility reading from the semen sample contained in the carrier.

9. The system according to claim 1, wherein the means for aspirating a sample comprises a pump which when actuated expels fluids from the chamber, and when subsequently released creates a partial vacuum in the chamber to draw in fluids, actuation of the pump being limited to aspirate a predetermined amount of fluid.

10. The system according to,claim 1, wherein the means for aspirating a sample comprises a finger-compressible, resilient air chamber, communicating with the sample chamber, which when compressed drives air through the sample chamber to expel fluids therefrom, and when subsequently released draws air from the sample chamber to create a partial vacuum therein to draw in fluids, compression of the air chamber being limited to aspirate a predetermined amount of fluid.

11. The system according to claim 1, further comprising:
    (a) a tray defining a plurality of uniform, closed cavities;
    (b) each cavity containing a precise amount of semen diluent; and
    (c) each cavity including means for inserting the shank of a carrier into the cavity to expel a semen sample from the carrier into the diluent and to stir them together, the mixture then being aspirated in the carrier for testing.

12. The system according to claim 11 wherein the cavities are closed by a frangible seal which can be breached by a shank of a carrier.

13. The system according to claim 1, further comprising a portable module in which the processor, the photon source means, and the plurality of photosensing means are incorporated, the module further comprising:

(a) a base including means for locating and seating a carrier, and (b) a wall closeable upon the base to sandwich a seated carrier therebetween, the base and wall being separable for cleaning, (c) the photon paths of a seated carrier being aligned between, and in communication with, the photon source means and respective photosensing means.

14. The system according to claim 13 wherein the base and wall open and close like a clamshell.

15. The system according to claim 13 wherein the photon source means is incorporated in the base, and wherein the photosensing means are incorporated in the wall.

16. The system according to claim 13 wherein the module is battery powered, and further comprising memory in which the processor can store the results of a plurality of analyses and other related information.

17. The system according to claim 13 a portable case for storing and carrying a plurality of modules.

18. The system according to claim 17 further comprising:

(a) for each module, a rechargeable battery for energizing the module, and (b) means, incorporated in the case, for recharging modules, (c) case processor means for downloading and storing information from modules' memories for further processing.

19. The system according to ,claims 1, wherein one of the plurality of photon paths is disposed at a point which contains no semen, and further comprising a second algorithm run by the processor which recognizes this photon path as a reference path and which uses the photosensing signal from the reference path and one of the other photon path signals to quantify the sperm density of a sample.

20. The system according to claim 1 wherein the shank is transparent, including a plurality of optically clear orifices, each photon path being defined by a pair of aligned orifices on opposite sides of the chamber.

21. A semen sample carrier comprising:

(a) a shank defining a chamber and an opening into the chamber for ingress and egress of a sperm sample, (b) manually operated means for aspirating a sample of sperm into the chamber, and (c) a plurality of distinct photon paths intersecting and passing through the chamber for photodetection of sperm characteristics.

* * * * *